(12) United States Patent
Feng et al.

(10) Patent No.: US 11,058,693 B1
(45) Date of Patent: Jul. 13, 2021

(54) PREPARATION METHOD OF WATER-SOLUBLE PHYTOSTEROL NANO-DISPERSION SYSTEM WITH INTESTINAL TARGETED RELEASE FUNCTION

(71) Applicant: ZHENGJIANG UNIVERSITY OF TECHNOLOGY, Hangzhou (CN)

(72) Inventors: Simin Feng, Hangzhou (CN); Peilong Sun, Hangzhou (CN); Ping Shao, Hangzhou (CN); Jiadan Yan, Hangzhou (CN); Dan Wang, Hangzhou (CN); Yuxin Sun, Hangzhou (CN)

(73) Assignee: ZHEJIANG UNIVERSITY OF TECHNOLOGY, Hangzhou (CN)

( * ) Notice: Subject to any disclaimer, the term of this patent is extended or adjusted under 35 U.S.C. 154(b) by 0 days.

(21) Appl. No.: 17/001,241

(22) Filed: Aug. 24, 2020

(30) Foreign Application Priority Data

Mar. 24, 2020 (CN) .......................... 202010211808.X

(51) Int. Cl.
*A61K 31/575* (2006.01)
*A61K 47/42* (2017.01)

(52) U.S. Cl.
CPC ............ *A61K 31/575* (2013.01); *A61K 47/42* (2013.01)

(58) Field of Classification Search
None
See application file for complete search history.

(56) References Cited

FOREIGN PATENT DOCUMENTS

| CN | 108606952 A | * | 10/2018 |
| CN | 109674053 A | * | 4/2019 |
| CN | 108606952 B |   | 1/2020 |

OTHER PUBLICATIONS

Google Translate. English Translation of CN 109674053 A. Obtained from https://patents.google.com/patent/CN108606952A/en?oq=CN+108606952+B on Dec. 14, 2020. Originally published in Chinese on Oct. 2, 2018, 8 printed pages. (Year: 2018).*

(Continued)

*Primary Examiner* — Isaac Shomer
(74) *Attorney, Agent, or Firm* — Muncy, Geissler, Olds & Lowe, P.C.

(57) ABSTRACT

The invention discloses a method for preparing a water-soluble phytosterol nano-dispersion system with intestinal targeted release function, which comprises the following steps: preparing a phytosterol solution; preparing an ethanol aqueous solution containing pectin; then adding zein to obtain a zein pectin solution; mixing the phytosterol solution and the zein pectin solution by means of ultrasonic treatment to obtain a nanoparticle dispersion liquid; rotavaping the nano-particle dispersion liquid to remove ethanol and water to obtain a zein/pectin loaded phytosterol nano-dispersion system. In this invention, not only an ultrasonic method and an anti-solvent method are adopted, but also a pectin component is added with zein as an entrapping agent, which ensures an effective entrapping of phytosterol by zein while further facilitating to form a more compact interface structure and improving a stability of the nano-dispersion system.

6 Claims, 3 Drawing Sheets

(56) References Cited

OTHER PUBLICATIONS

ZK Mukhidinov, GF Kasimova, DT Bobokalonov, DKh. Khalikov, Khl Teshaev, MD Khalikova, and LS Liu. "Pectin-Zein Microspheres as Drug Delivery Systems." Pharmaceutical Chemistry Journal vol. 44, No. 10, 2011, pp. 564-567. (Year: 2011).*

F-Z Zhou, X-N Huang, Z-L Wu, S-W Yin, J-H Zhu, C-H Tang, andX-Q Yang. "Fabrication of Zein/Pectin Hybrid Particle-Stabilized Pickering High Internal Phase Emulsions with Robust and Ordered Interface Architecture." Journal of Agricultural and Food Chemistry, vol. 66, 2018, p. 11113-11123. (Year: 2018).*

LinShu Liu, Marshall L. Fishman, Kevin B. Hicks, Meir Kende, and Gordon Ruthel. "Pectin/Zein Beads for Potential Colon-Specific Drug Delivery: Synthesis and in Vitro Evaluation." Drug Delivery, vol. 13, 2006, pp. 417-423. (Year: 2006).*

Sanko Nguyen, Siv Jorunn Alund, Marianne Hiorth, Anna-Lena Kjøniksen, Gro Smistad. "Studies on pectin coating of liposomes for drug delivery." Colloids and Surfaces B: Biointerfaces 88 (2011) 664-673. (Year: 2011).*

Google Patents. English Translation of CN-108606952-A. https://patents.google.com/patent/CN108606952A/en?oq=CN+108606952+A accessed by examiner on Mar. 23, 2021, originally published in Chinese on Oct. 2, 2018, pp. 1-7. (Year: 2018 ).*

* cited by examiner

PREPARATION METHOD OF WATER-SOLUBLE PHYTOSTEROL NANO-DISPERSION SYSTEM WITH INTESTINAL TARGETED RELEASE FUNCTION

TECHNICAL FIELD

The invention relates to a technical field of preparation of water-soluble phytosterol, in particular to a method for preparing a water-soluble phytosterol nano-dispersion system with intestinal targeted release function.

BACKGROUND ART

A molecular structure of phytosterol is similar to that of cholesterol, and it is an effective way to reduce cholesterol by consuming foods rich in phytosterol. However, since phytosterols are mostly insoluble in fat and insoluble in water, it is difficult to add phytosterols directly into food or medicine, which affects its application.

Currently, researchers have adopted emulsification, entrapping, loading and other modification methods to significantly enhance a water solubility of phytosterol, and adopted esterification and other operations to increase its fat solubility, making it applicable in more fields.

Zein is a main storage protein in corn, which can be self-assembled into nanoparticles with various medium structures. Zein, which is one of the few hydrophobic biopolymers, has been widely used as a delivery vehicle of a hydrophobic active substance.

A method for preparing a zein loaded phytosterol nano emulsion is disclosed in Chinese Patent No. CN108606952B, which comprises the following steps: firstly, dissolving phytosterol in an organic solvent, then dropwise adding the phytosterol into an alcohol solution of zein under ultrasonic conditions for mixing, and continuously performing an ultrasonic treatment after mixing to obtain nanoparticle dispersion liquid; rotavaping the nanoparticle dispersion liquid to remove the organic solvent, and then adding deionized water to form a zein loaded phytosterol nano emulsion. The method not only presents a short preparation time and a high efficiency, but also provides an emulsion with properties of gravity stability, small particle size and high entrapping rate.

However, there are still some problems in the above-mentioned nano emulsion, for example, zein nanoparticles are highly sensitive to ionic strength and pH value, and will rapidly aggregate and precipitate even at low salt content, resulting in a poor transportation effect during digestion.

Therefore, it is necessary to do further research on the above nano-emulsion to solve the above technical problems.

SUMMARY

An object of the present invention is to provide a method for preparing a water-soluble phytosterol nano-dispersion system with intestinal targeted release function, and this method not only presents a short preparation time and a high efficiency, provides a dispersion system with properties of small particle size and gravity stability, and it also improves a water solubility of phytosterol, broadens an application range of the dispersion system and increases its bioavailability.

The specific technical scheme is as follows:

Method for preparing a water-soluble phytosterol nano-dispersion system with intestinal targeted release function comprises the following steps:

(1) dissolving phytosterol in absolute ethanol to obtain a phytosterol solution;

(2) pre-dissolving pectin in deionized water, and then adding with ethanol to obtain an ethanol aqueous solution containing pectin; adding zein into the ethanol aqueous solution to obtain a zein pectin solution;

(3) mixing the phytosterol solution in the step (1) and the zein pectin solution in the step (2) by means of ultrasonic treatment to obtain a nanoparticle dispersion liquid;

(4) rotavaping the nanoparticle dispersion liquid to remove the organic solvent and water to obtain a water-soluble phytosterol nano-dispersion system.

Pectin, by which the self-assembly behavior of zein can be well controlled, is suitable to be used as a surface adsorption material for nanoparticles formed by zein so as to improve a wettability of zein surface; at the same time, it can effectively reduce a sensitivity of zein to ionic strength, pH and human digestive tract environment, and improve its stability.

In this invention, not only an ultrasonic method and an anti-solvent method are adopted, but also a pectin component is added with zein as an entrapping agent, which ensures an effective entrapping of phytosterol by zein while further facilitating a more compact interface structure and improving a stability of the nano-dispersion system.

Further, in the ethanol aqueous solution in the step (2) contains 80-90% ethanol by volume.

It is found that a ratio of pectin to zein will affect a particle size, entrapping rate and loading capacity of the nano-dispersion system. Further, in the zein pectin solution in step (2), a mass ratio of pectin to zein is 1-2:10.

It is found that different ultrasonic methods will have an impact on a particle size for the nano solution. Further, in the step (3), ultrasonic treatment conditions are as follows: a continuous ultrasonic treatment using a probe ultrasonic processor with an ultrasonic frequency of 15-25 kHz, a power of 150~250 W, and an lasted time of 1-3 min.

Preferably, the ultrasonic frequency is 20 KHZ, the power is 200 W, and the lasted time is 2 min.

Further, after the continuous ultrasonic treatment is finished, the ultrasonic treatment is continued with a pulse mode, with a pulse frequency of "1 s" and a lasted time of 0.5~1.5 min. More preferably, the lasted time is 1 min.

Further, in the nanoparticle dispersion liquid in the step (3), a mass ratio of phytosterol, pectin and zein is 1:0.1-12.5:1-25. More preferably, that ratio of pectin to zein is 1:10.

Further, in the step (4), a temperature for the rotavaping is 40-50° C., with a rotating speed of 50-60 rpm.

Compared with the prior art, the invention has the following beneficial effects:

(1) In this invention, not only an ultrasonic method and an anti-solvent method are adopted, but also a pectin component is added with zein as an entrapping agent, which ensures an effective entrapping of phytosterol by zein while further reducing a sensitivity of zein to ionic strength, pH and human digestive tract environment, facilitating to form a more compact interface structure and improving a stability of the nano-dispersion system.

(2) the present invention not only presents a short preparation time and a high efficiency, provides a dispersion system with properties of small particle size and gravity stability, and it also improves a water solubility of phytosterol, broadens an application range of the dispersion system and increases its bioavailability.

(3) By adding pectin, phytosterol can be directionally released in small intestine by using an ion switch in the method of the invention, which is of great significance.

DETAILED DESCRIPTION OF PREFERRED EMBODIMENTS

Figure 1:
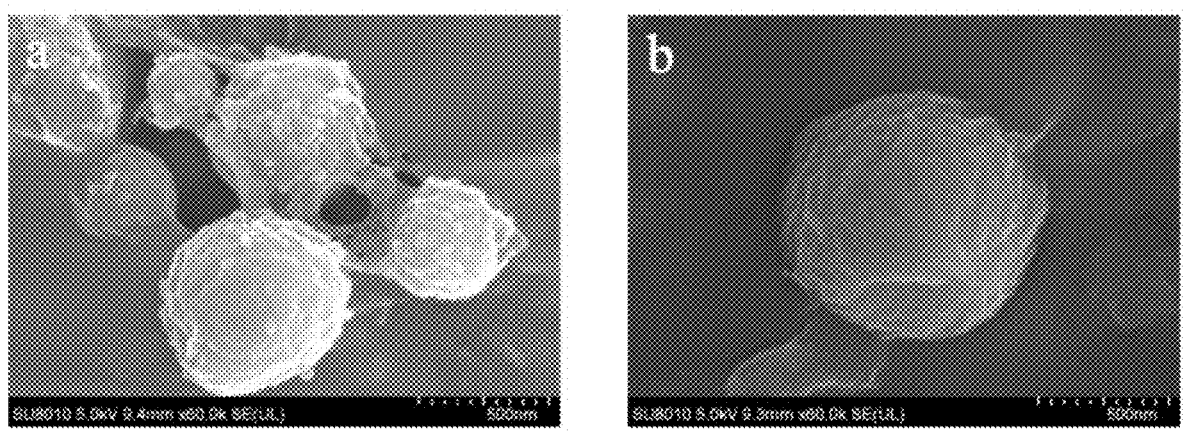
FIG. 1 is a field emission surface scanning electron microscope image of a nano-dispersion system prepared in Example 1 and Comparative Example 1;
where a is the nano-dispersion system of Example 1, and b is the nano-dispersion system of Comparative Example 1.

The invention which is implemented according to inventive technical schemes will be further set forth in connection with specific examples below and detailed implementations and operation steps will be given, but the protection scope of the invention is not intended to be limited to the following examples. The experimental methods for which specific conditions are not indicated in the following examples are generally in accordance with conventional conditions. In the following examples, stigmasterol in phytosterol was adopted for corresponding experiments.

Example 1

A method for preparing a water-soluble phytosterol nano-dispersion system with intestinal targeted release function comprises the following steps:

(1) dissolving 10 mg stigmasterol in 5 mL absolute ethanol to formulate a stigmasterol solution with a mass concentration of 2 mg/mL, and then place the stigmasterol solution in a 45° C. water bath to facilitate a dispersion.

(2) pre-dissolving 5 mg pectin in 10 mL deionized water, adding with ethanol into the solution to a volume of 50 mL to obtain 80% (by volume) aqueous ethanol solution containing 0.1 mg/mL (by mass) pectin; and then, adding 50 mg zein to the above 80% ethanol aqueous solution to obtain a zein pectin solution.

(3) mixing the stigmasterol solution in step (1) with the zein pectin solution in step (2) by means of ultrasonic treatment, and preparing a nano-dispersion liquid (i.e., nano particles);
Ultrasonic conditions were as follows: FS-1200pv probe ultrasonic processor with a ultrasonic frequency of 20 KHZ, a power of 200 W, a ultrasonic pulse mode of "1 s", and a lasted time of 2 min; another 1 min ultrasonic treatment after the 2-min one).

(4) rotavaping (RE-2000A vacuum rotary evaporator) the ultrasound-treated nano-dispersion liquid at 45° C. and 55 rpm to remove ethanol and excess water until the volume of the solution being 50 mL, and thus obtaining the final water-soluble phytosterol nano-dispersion system.

Figure 2:
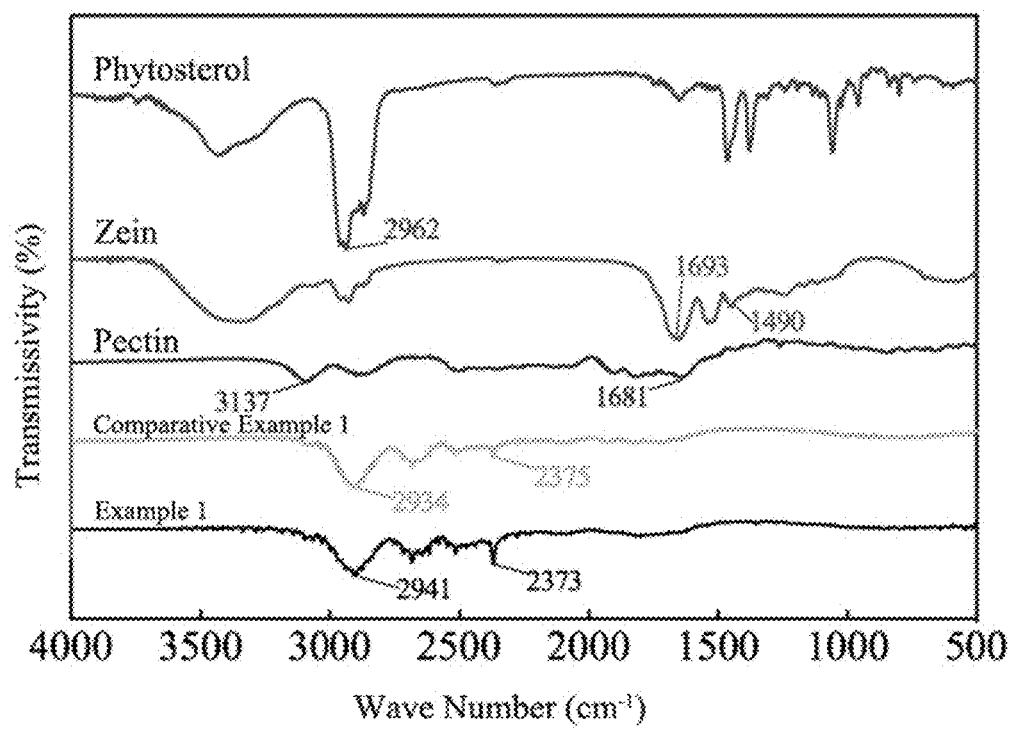
FIG. 2 is the Fourier infrared spectra of the nano-dispersion system of Example 1, the nano-dispersion system of Comparative Example 1, phytosterol, zein and pectin.
Figure 3:
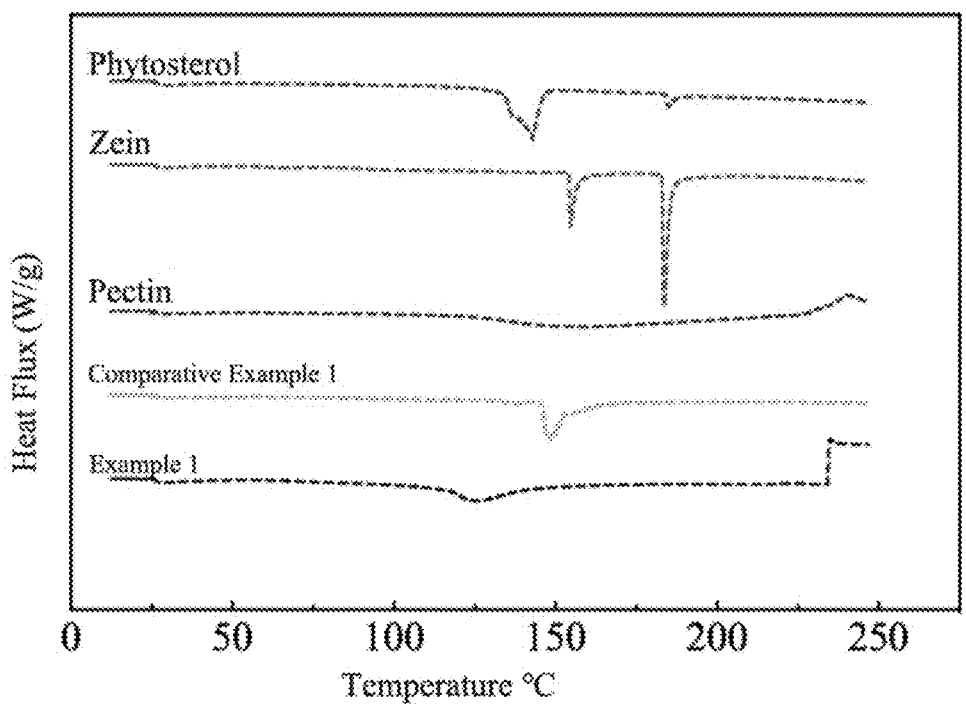
FIG. 3 is a differential scanning calorimetry thermogram of the nano-dispersion system of Example 1, the nano-dispersion system of Comparative Example 1, phytosterol, zein and pectin.

20 mL of the above nano-dispersion system was placed into a sample bottle, and a field emission surface scanning electron microscope image, Fourier infrared spectra and differential scanning calorimetry thermogram were obtained, and the electric potential, particle size (Omni dynamic light scattering particle size analyzer), entrapping rate and loading capacity were measured, and the results were shown in Table 1 and FIGS. 1-3.

Example 2

A method for preparing a water-soluble phytosterol nano-dispersion system with intestinal targeted release function comprises the following steps:

(1) dissolving 10 mg stigmasterol in 5 mL absolute ethanol to formulate a stigmasterol solution with a mass concentration of 2 mg/mL, and then place the stigmasterol solution in a 45° C. water bath to facilitate a dispersion.

(2) pre-dissolving 10 mg pectin in 10 mL deionized water, adding with ethanol into the solution to a volume of 50 mL to obtain 80% (by volume) aqueous ethanol solution containing 0.2 mg/mL (by mass) pectin; and then, adding 50 mg zein to the above 80% ethanol aqueous solution to obtain a zein pectin solution.

(3) mixing the stigmasterol solution in step (1) with the zein pectin solution in step (2) by means of ultrasonic treatment, and preparing a nano-dispersion liquid (i.e., nano particles);
Ultrasonic conditions were as follows: FS-1200pv probe ultrasonic processor with a ultrasonic frequency of 20 KHZ, a power of 200 W, a ultrasonic pulse mode of "1 s", and a lasted time of 2 min; another 1 min ultrasonic treatment after the 2-min one).

(4) rotavaping (RE-2000A vacuum rotary evaporator) the ultrasound-treated nano-dispersion liquid at 45° C. and 55 rpm to remove ethanol and excess water until the volume of the solution being 50 mL, and thus obtaining the final water-soluble phytosterol nano-dispersion system.

20 mL of the above nano-dispersion system was placed into a sample bottle, and the electric potential, particle size (Omni dynamic light scattering particle size analyzer), entrapping rate and loading capacity were measured, and the results were shown in Table 1.

Comparative Example 1

A method for preparing a zein loaded stigmasterol nano-dispersion system specifically comprises the following steps:

(1) dissolving 10 mg stigmasterol in 5 mL absolute ethanol to formulate a stigmasterol solution with a mass concentration of 2 mg/mL, and then place the stigmasterol solution in a 45° C. water bath to facilitate a dispersion.

(2) Adding 50 mg zein into 80% (by volume) ethanol aqueous solution to obtain a zein solution.

(3) mixing the stigmasterol solution in step (1) with the zein pectin solution in step (2) by means of ultrasonic treatment, and preparing a nano-dispersion liquid (i.e., nano particles);
Ultrasonic conditions were as follows: FS-1200pv probe ultrasonic processor with a ultrasonic frequency of 20 KHZ, a power of 200 W, a ultrasonic pulse mode of "1 s", and a lasted time of 2 min; another 1 min ultrasonic treatment after the 2-min one).

(4) rotavaping (RE-2000A vacuum rotary evaporator) the ultrasound-treated nano-dispersion liquid at 45° C. and 55 rpm to remove ethanol and excess water until the volume of the solution being 50 mL, and thus obtaining the final zein-loaded stigmasterol nano-dispersion system.

20 mL of the above nano-dispersion system was placed into a sample bottle, and a field emission surface scanning electron microscope image, Fourier infrared spectra and differential scanning calorimetry thermogram were obtained, and the electric potential, particle size (Omni dynamic light scattering particle size analyzer), entrapping rate and loading capacity were measured, and the results were shown in Table 1 and FIGS. 1-3.

Comparative Example 2

This comparative example is exactly the same as Example 1 except that the amount of pectin added is 25 mg, and the results are shown in Table 1.

Comparative Example 3

(1) dissolving 10 mg stigmasterol in 5 mL absolute ethanol to formulate a stigmasterol solution with a mass concentration of 2 mg/mL, and then place the stigmasterol solution in a 45° C. water bath to facilitate a dispersion.

(2) Adding 50 mg zein into 80% (by volume) ethanol aqueous solution to obtain a zein solution.

(3) mixing the stigmasterol solution in step (1) with the zein solution in step (2) by means of ultrasonic treatment, and preparing a nano-dispersion liquid;

Ultrasonic conditions were as follows: FS-1200pv probe ultrasonic processor with a ultrasonic frequency of 20 KHZ, a power of 200 W, a ultrasonic pulse mode of "1 s", and a lasted time of 2 min; another 1 min ultrasonic treatment after the 2-min one.

(4) rotavaping (RE-2000A vacuum rotary evaporator) the ultrasound-treated nano-dispersion liquid at 45° C. and 55 rpm to remove ethanol and excess water until the volume of the solution being 50 mL.

(5) adding 5 mg pectin into the dispersion system obtained in step (4), and magnetic stirring overnight to complete an electrostatic adsorption.

20 mL of the above nano-dispersion system was placed into a sample bottle, and the electric potential, particle size (Omni dynamic light scattering particle size analyzer), entrapping rate and loading capacity were measured, and the results were shown in Table 1.

TABLE 1 electric potential, particle size, sterol entrapping rate and loading capacity of dispersion systems with different pectin/zein ratio

| | Particle Size | Electric Potential | Entrapping Rate | Loading Capacity |
|---|---|---|---|---|
| Example 1 (1:10) | 584.40 ± 69.55 nm | −38.32 ± 0.23 mV | 84.96 ± 3.28% | (15.45 ± 0.59 g)/100 g |
| Example 2 (2:10) | 803.06 ± 32.19 nm | −11.65 ± 0.52 mV | 75.64 ± 1.45% | (12.61 ± 0.24 g)/100 g |
| Comparative Example 1 (0:10) | 374.05 ± 54.30 nm | 38.57 ± 0.36 mV | 90.16 ± 2.05% | (18.02 ± 0.4 g)/100 g |
| Comparative Example 2 (5:10) | 1230.94 ± 255.74 nm | −8.86 ± 1.48 mV | 71.07 ± 1.63% | (9.48 ± 0.22 g)/100 g |
| Comparative Example 3 (1:10, electrostatic adsorption) | 867.24 ± 67.13 nm | −8.78 ± 0.56 mV | 65.24 ± 5.46% | (11.86 ± 0.37 g)/100 g |

It can be seen from Table 1 that the nanoparticles were negatively charged after pectin was added, which indicated that a sugar chain of pectin extended outside the zein particles, instead of simply wrapping zein on the outer layer of the particles, thus forming a more compact interface structure and improving the stability of the nano-dispersion system.

When the ratio of pectin to zein increased from 2:10 to 5:10, the particle size increased significantly and the Zeta electric potential decreased significantly, which meant that the stability of dispersion system was decreased. The decrease of the stability was due to the increase of the particle size caused by a high-concentration pectin solution, which leaded to an aggregation in the nano-dispersion system. The decrease of the entrapping rate and loading capability indicated that a stronger static electricity was provided due to excess pectin, which limited an entrapping behavior of zein particles. At the same time, the particle size of non-entrapped stigmasterol crystals would increases.

In Example 1, the pectin solution was firstly added to the zein solution for premixing and then ultrasonic treatment, which could effectively improve the stigmasterol entrapping rate and loading capacity, and the stability of the dispersion system. The premixing of the pectin solution in Example 1 effectively improved a driving force for the anti-solvent method. Compared with Comparative Example 1, in Example 1 and after the pectin solution and the zein solution were premixed, nanoparticles could be spontaneously formed by zein, along with pectin, due to its self-assembly ability, which shortened a preparation process and provided characteristics of low energy consumption and high efficiency.

As shown in FIG. 1a, for the stigmasterol nanoparticles shown in the field emission scanning electron microscope image, an elastic network gel was formed outside the nanoparticles by pectin. As shown in FIG. 1b, the nanoparticles shown in the field emission scanning electron microscope image in Comparative Example 1 were spherical particles with a regular surface morphology but without a gel network structure.

As shown in FIG. 2, it was found in Fourier transform infrared spectra that a broad peak at 3137 cm$^{-1}$ moved to 2941 cm$^{-1}$ due to a stretching vibration of O—H in pectin in a complex formed therewith, indicating that a hydrogen bond was formed between an amide group of glutamine in zein and a carboxyl group or hydroxyl group in pectin. The broad peak at 3137 cm$^{-1}$ of pectin moved to 2941 cm$^{-1}$ Example 1, while the broad peak of Comparative Example 1 was at 2934 cm$^{-1}$, which indicated that the adding of pectin improved a wettability of zein.

As shown in FIG. 3, the differential scanning calorimetry thermogram showed that a characteristic peak of stigmasterol can be well suppressed in Example 1, which indicated that the crystal of stigmasterol has been transformed into a microcrystalline state in Example 1, and stigmasterol was entrapped. Meanwhile, in a curve of Example 1, the characteristic peak of zein was completely suppressed, indicating that zein and stigmasterol were successfully entrapped by pectin. An enthalpy value for heat absorption peak in Comparative Example 1 was 67.83 J/g, which was higher than 42.45 J/g of Example 1, which indicated that the stability of Comparative Example 1 is worse than that of Example 1, and damage to particles by a temperature rising process is greater.

Figure 4:
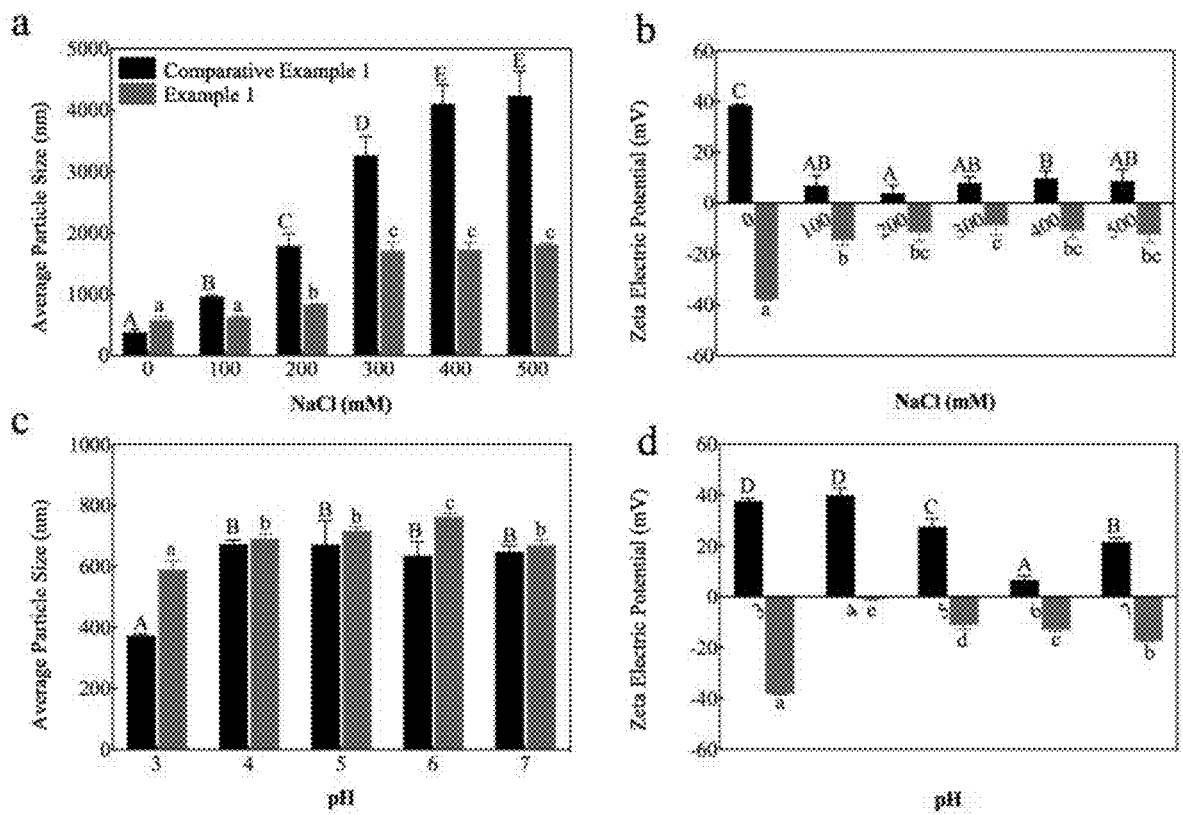
FIG. 4 shows a particle size and electric potential of Example 1 and Comparative Example 1 under different ionic strength and pH conditions.
Figure 5:
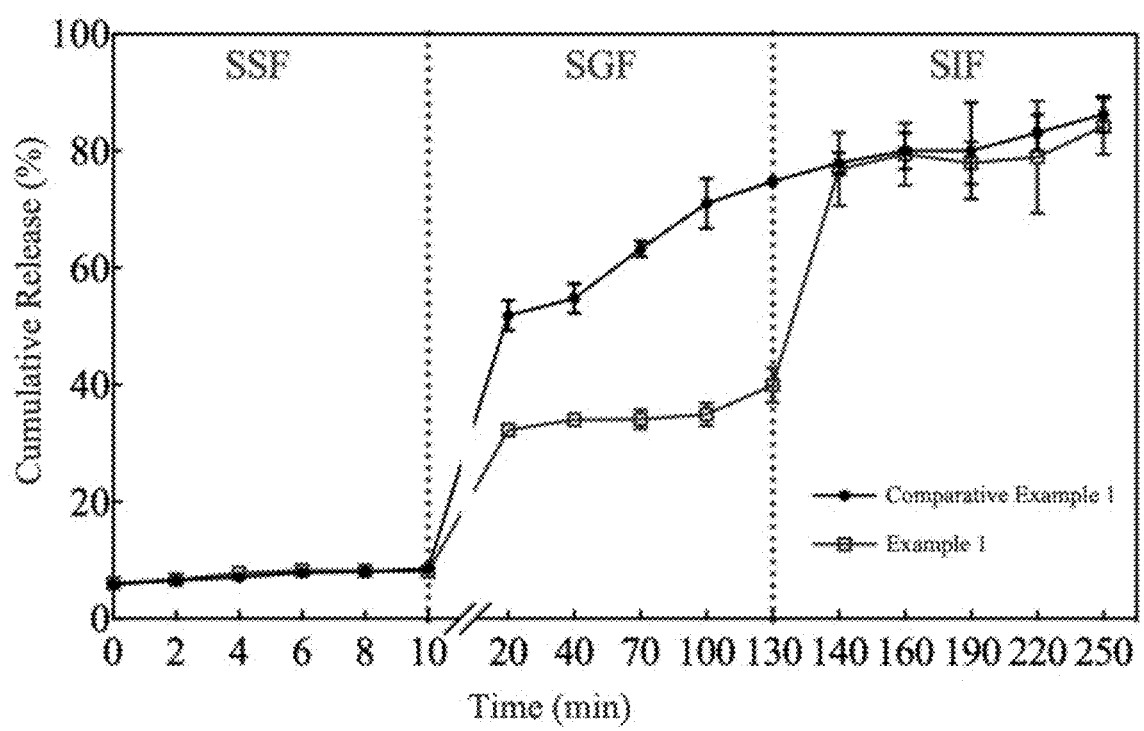
FIG. 5 shows the change of a phytosterol release rate in vitro simulated digestion of Example 1 and Comparative Example 1;
where SSF is simulated oral fluid, SGF is simulated gastric fluid and SIF is simulated small intestine fluid.

In addition, the ionic strength and pH value of the nano-dispersion system prepared in Example 1 and Comparative Example 1 were measured to discuss the influence of ionic strength and pH value on the stability of the nano-dispersion system (FIG. 4); and a vitro release of stigmasterol from the nano-dispersion system was evaluated in an environment simulating gastrointestinal tract (FIG. 5).

The method were specifically as follows:

(1) measuring the ionic strength and pH value of the nano-dispersion system prepared in Example 1 and Comparative Example 1:

The newly prepared nano-dispersion was diluted 10 times with a proper amount of 1 mol/L NaCl solution or deionized water to obtain samples with different final salt concentrations (0, 100, 200, 300 and 400 mmol/L). For a pH test, the diluted nano-dispersion system was adjusted to different pH values (3-7). The nano-dispersion system was stored overnight at room temperature, and then the particle size and Zeta electric potential were measured respectively.

(2) determining the release of stigmasterol in the nano-dispersion system prepared in Example 1 and Comparative Example 1 under the simulated gastrointestinal environment:

A mechanism of stigmasterol release from the nano-dispersion system was evaluated by simulating gastrointestinal tract. The newly prepared nano-dispersion system was concentrated to 20 mL at 45° C. by using a vacuum rotary evaporator, and then transferred to a dialysis bag with a molecular weight cut-off of 8000-12,000 Da. The dialysis bags were immersed in 80 mL simulated gastrointestinal fluid. The whole digestion process was carried out in a water bath oscillator at 37° C. All solutions were required to be preheated in a water bath at 37° C. before mixing.

I) Oral Phase

Simulated saliva (SSF) was prepared by dissolving 1.6 g NaCl, 0.2 g KCl and 0.6 g mucin in 1 L deionized water, and then the pH was adjusted to 6.8 with a 0.1 moL/L NaOH solution. The dialysis bag was immersed in 80 mL SSF. The above system was shaken in a water bath shaker (37° C.) at 100 rpm for 10 minutes. At each time point of 0, 2, 4, 6, 8 and 10 minutes, 5 mL of release medium was taken out from the incubation bath.

II) Gastric Phase

Simulated gastric fluid (SGF) was prepared by dissolving 2 g NaCl, 7 mL concentrated HCl and 3.2 g pepsin in 1 L deionized water and then the pH was adjusted to 1.2 with a 0.1 moL/L HCl solution. The dialysis bag transferred from SSF was immersed in 80 mL SGF. The above system was shaken in a water bath shaker (37° C.) at 100 rpm for 120 minutes. At each time point of 10, 30, 60, 90 and 120 minutes, 5 mL of release medium was taken out from the incubation bath.

III) Small Intestine Phase

Simulated small intestine fluid (SIF) was prepared by dissolving 6.8 g $K_2HPO_4$, 8.8 g NaCl, 5 g bile salt and 3.2 g pancreatin in 1 L deionized water and then the pH is adjusted to 7.0. The dialysis bag transferred from SGF was immersed in 80 mL SIF. The above system was shaken in a water bath shaker (37° C.) at 100 rpm for 120 minutes. At each time point of 10, 30, 60, 90 and 120 minutes, 5 mL of release medium was taken out from the incubation bath.

About 5 mL of n-hexane was added to the release medium to dissolve the released stigmasterol. An upper layer of n-hexane was transferred to a 15 mL centrifuge tube and dried by a vacuum centrifugal concentrator. Then, the dried stigmasterol was redissolved by absolute ethanol, and a stigmasterol content was measured. The cumulative release Q (%) of stigmasterol was calculated by the following formula:

$$Q=(M_i)/M_t \times 100\%$$

where $M_1$ was the content of stigmasterol released at each sampling time and $M_t$ was the content of stigmasterol in the medium at each sampling time.

The results were shown in FIGS. 4 and 5.

As shown in FIG. 4, it could be found from effects of different ionic strength and pH conditions on the particle size and electric potential that the adding of pectin reduces the sensitivity to aggregation and improves the stability under different environmental conditions. Compared with Example 1, an aggregation was more prone to occur under different environmental conditions for Comparative Example 1. The reason was that the added counterions ($Na^+$ or $Cl^-$) would neutralize charges in zein nanoparticles, which would produce an electrostatic shielding effect to reduce an electrostatic repulsion which was a main factor for the forming of the nano-dispersion system.

As shown in FIG. 5, it could be found in a vitro simulated digestion that since stigmasterol mainly was absorbed in the small intestine and suppressed the absorption of cholesterol in the intestine to play a physiological role, phytosterol can be directionally released in small intestine by using an ion switch by adding pectin, which is of great significance. In a simulated gastrointestinal digestion, zein might be hydrolyzed by pepsin and pancreatin, thus destroying the structure of nanoparticles, resulting in the release of stigmasterol of Comparative Example 1 in SGF and SIF. However, the pectin solution was acidic and could not be digested by pepsin in SGF, so pectin could exist stably under acidic conditions; meanwhile, under high acidic conditions (pH 1.5) and because of the losing of some negative charges for pectin molecules, an adhesion between pectin molecules and the surface of zein nanoparticles decreased, resulting in a local resistance of pectin to SGF; and compared with Comparative Example 1, less stigmasterol could be released in SGF in Example 1, so that stigmasterol could be transferred to SIF for releasing.

From the above Examples 1 and 2 and Comparative Examples 1-3, it could be seen that when the mass ratio of pectin to zein was 1:10, the mixing was carried out for 2 min by means of ultrasonic treatment with a power of 200 W, followed by a pulse ultrasonic treatment for 1 min with an ultrasonic mode of "1 s", the prepared nano-dispersion system is stable (an absolute value of Zeta electric potential is greater than 30 mV), with a small average particle size and a large entrapping rate; in addition, due to the existence of pectin, the stability of nanoparticles in different environments and simulated digestion conditions were improved, and phytosterol can be directionally released in small intestine by using an ion switch, which is of great significance.

The invention claimed is:

1. A method for preparing a water-soluble phytosterol nano-dispersion system with intestinal targeted release function, wherein the phytosterol is stigmasterol, wherein the method comprises the following steps:

(1) dissolving the stigmasterol in absolute ethanol to obtain a stigmasterol solution;

(2) pre-dissolving pectin in deionized water, and then adding with ethanol to obtain an ethanol aqueous solution containing pectin; adding zein into the ethanol aqueous solution to obtain a zein pectin solution, wherein a mass ratio of pectin to zein is 1:10;

(3) mixing the stigmasterol solution in the step (1) and the zein pectin solution in the step (2) by means of ultrasonic treatment to obtain a nanoparticle dispersion liquid;

(4) rotavaping the nanoparticle dispersion liquid to remove the organic solvent and water to obtain a water-soluble stigmasterol nano-dispersion system.

2. The method for preparing a water-soluble phytosterol nano-dispersion system with intestinal targeted release function according to claim 1, wherein the ethanol aqueous solution in step (2) contains 80-90% ethanol by volume.

3. The method for preparing a water-soluble phytosterol nano-dispersion system with intestinal targeted function according to claim 1, wherein in the step (3), the ultrasonic treatment conditions are as follows: a continuous ultrasonic treatment using a probe ultrasonic processor with an ultrasonic frequency of 15-25 kHz, a power of 150-250 W, and a lasted time of 1-3 min.

4. The method for preparing a water-soluble phytosterol nano-dispersion system with intestinal targeted function according to claim 3, wherein after the continuous ultrasonic treatment is finished, the ultrasonic treatment is continued with a pulse mode, with a pulse frequency of 1 pulse per second and a lasted time of 0.5~1.5 min.

5. The method for preparing a water-soluble phytosterol nano-dispersion system with intestinal targeted function according to claim 1, wherein in the nanoparticle dispersion liquid in the step (3), a mass ratio of stigmasterol, pectin and zein is 1:0.5:5.

6. The method for preparing a water-soluble phytosterol nano-dispersion system with intestinal targeted function according to claim 1, wherein in the step (4), a temperature for the rotavaping is 40-50° C., with a rotating speed of 50-60 rpm.

* * * * *

UNITED STATES PATENT AND TRADEMARK OFFICE
CERTIFICATE OF CORRECTION

PATENT NO. : 11,058,693 B1
APPLICATION NO. : 17/001241
DATED : July 13, 2021
INVENTOR(S) : Simin Feng et al.

Page 1 of 1

It is certified that error appears in the above-identified patent and that said Letters Patent is hereby corrected as shown below:

On the Title Page

(71) Applicant reads:
"ZHENGJIANG UNIVERSITY OF TECHNOLOGY, Hangzhou (CN)"
Should read:
--ZHEJIANG UNIVERSITY OF TECHNOLOGY, Hangzhou (CN)--

Signed and Sealed this
Twenty-first Day of September, 2021

Drew Hirshfeld
*Performing the Functions and Duties of the
Under Secretary of Commerce for Intellectual Property and
Director of the United States Patent and Trademark Office*